(12) United States Patent
Buschhaus et al.

(10) Patent No.: US 12,059,331 B2
(45) Date of Patent: Aug. 13, 2024

(54) SHAPED TAMPON

(71) Applicant: Johnson & Johnson GmbH, Neuss (DE)

(72) Inventors: Mirko Buschhaus, Essen (DE); David L. Kimball, Flemington, NJ (US); Lionel Robbe, Cologne (DE)

(73) Assignee: Johnson & Johnson GmbH, Neuss (DE)

( * ) Notice: Subject to any disclaimer, the term of this patent is extended or adjusted under 35 U.S.C. 154(b) by 786 days.

(21) Appl. No.: 17/022,306

(22) Filed: Sep. 16, 2020

(65) Prior Publication Data

US 2021/0093486 A1    Apr. 1, 2021

Related U.S. Application Data

(60) Provisional application No. 62/907,215, filed on Sep. 27, 2019.

(51) Int. Cl.
*A61F 13/20* (2006.01)
*A61F 13/26* (2006.01)
*A61F 13/34* (2006.01)

(52) U.S. Cl.
CPC ...... *A61F 13/2034* (2013.01); *A61F 13/2037* (2013.01); *A61F 13/26* (2013.01); *A61F 13/34* (2013.01)

(58) Field of Classification Search
CPC .. A61F 13/2034; A61F 13/2037; A61F 13/26; A61F 13/34; A61F 13/20; A61F 13/2022; A61F 13/2025; A61F 13/2028; A61F 13/208

See application file for complete search history.

(56) References Cited

U.S. PATENT DOCUMENTS

| | | |
|---|---|---|
| 3,854,481 A | 12/1974 | Messing |
| 4,212,301 A | 7/1980 | Johnson |
| 4,326,527 A | 4/1982 | Wollangk et al. |
| 4,627,849 A | 12/1986 | Walton et al. |
| 5,153,971 A | 10/1992 | Van Iten |
| 5,370,633 A | 12/1994 | Villalta |
| 5,659,934 A | 8/1997 | Jessup et al. |
| 6,310,269 B1 | 10/2001 | Friese et al. |
| 7,120,977 B2 | 10/2006 | Bittner et al. |
| 7,736,572 B2 | 6/2010 | Gilbert et al. |
| 7,740,787 B2 | 6/2010 | Hubbard, Jr. et al. |
| 7,867,209 B2 | 1/2011 | Jorgensen et al. |
| 7,981,347 B2 | 7/2011 | Hubbard, Jr. et al. |
| 8,082,639 B2 | 12/2011 | Rolli |
| 8,293,968 B2 | 10/2012 | Schmidt-Först et al. |
| 8,460,262 B2 | 6/2013 | Fung et al. |
| 8,474,114 B2 | 7/2013 | Rolli |

(Continued)

FOREIGN PATENT DOCUMENTS

| | | | |
|---|---|---|---|
| CN | 106999327 A | * | 11/2015 |
| EP | 1459720 A | | 9/2004 |

(Continued)

OTHER PUBLICATIONS

International search report and written opinion dated Nov. 25, 2020, for international application PCT/EP2020/076935).

*Primary Examiner* — Catharine L Anderson

(57) ABSTRACT

A shaped tampon with a groove pattern and a combination of external shapes varying radially and longitudinally.

17 Claims, 4 Drawing Sheets

(56) References Cited

U.S. PATENT DOCUMENTS

| | | |
|---|---|---|
| 8,518,005 B2 | 8/2013 | Handel et al. |
| 8,574,210 B2 | 11/2013 | Van Ingelgem et al. |
| 8,684,987 B2 | 4/2014 | Hasse et al. |
| 8,735,647 B2 | 5/2014 | Schoelling |
| 8,827,975 B2 * | 9/2014 | Kimball ............. A61F 13/2034 604/385.18 |
| 8,834,439 B2 | 9/2014 | Kimball et al. |
| 9,155,666 B2 | 10/2015 | Smet et al. |
| 9,610,201 B2 * | 4/2017 | Schmidt-Foerst ........................ A61F 13/2051 |
| 9,622,919 B2 * | 4/2017 | Pelley ................. B29C 43/027 |
| 9,795,518 B2 | 10/2017 | Pelley |
| 2003/0176845 A1 | 9/2003 | Kollwitz |
| 2004/0199137 A1 | 10/2004 | Lamb et al. |
| 2004/0226152 A1 | 11/2004 | Prosise et al. |
| 2005/0113787 A1 | 5/2005 | Carlin |
| 2007/0234532 A1 | 10/2007 | Gilbert et al. |
| 2008/0065041 A1 | 3/2008 | Stan et al. |
| 2008/0119811 A1 | 5/2008 | Gilbert et al. |
| 2008/0275417 A1 | 11/2008 | Gilbert et al. |
| 2009/0082712 A1 | 3/2009 | Hasse et al. |
| 2010/0102481 A1 | 4/2010 | Hubbard, Jr. et al. |
| 2013/0018342 A1 | 1/2013 | Schmidt-Forst |
| 2013/0072892 A1 | 3/2013 | Hasse et al. |
| 2014/0000628 A1 | 1/2014 | Avery, Jr. et al. |
| 2014/0265026 A1 | 9/2014 | Schoelling |

FOREIGN PATENT DOCUMENTS

| | | | |
|---|---|---|---|
| EP | 1459720 | B | 4/2005 |
| EP | 1622556 | B | 2/2006 |
| EP | 1759678 | A | 3/2007 |
| EP | 1485054 | B | 8/2007 |
| EP | 1622557 | B | 11/2007 |
| EP | 1485055 | B | 12/2007 |
| EP | 1601322 | B | 12/2008 |
| EP | 1267782 | B | 1/2012 |
| EP | 1485053 | B | 10/2012 |
| EP | 2349158 | B | 7/2013 |
| EP | 2712594 | B | 9/2015 |
| EP | 2712596 | B | 8/2016 |
| EP | 2900467 | B | 6/2017 |
| EP | 2712595 | B | 7/2017 |
| WO | WO 2004/080362 | A | 9/2004 |
| WO | WO 2004/100846 | A | 11/2004 |
| WO | WO 2004/100847 | A | 11/2004 |
| WO | WO 2005/046548 | A | 5/2005 |
| WO | WO 2005/046549 | A | 5/2005 |
| WO | WO 2008/056339 | A | 5/2008 |
| WO | WO 2009/040737 | A | 4/2009 |
| WO | WO 2014/004798 | A | 1/2014 |
| WO | WO 2018/220587 | A | 12/2018 |

* cited by examiner

SHAPED TAMPON

CROSS-REFERENCE TO RELATED APPLICATIONS

This application claims the benefit of U.S. Provisional application 62/907,215 filed on Sep. 27, 2019, the complete disclosure of which is hereby incorporated herein by reference for all purposes.

TECHNICAL FIELD OF THE INVENTION

The present invention relates to absorbent intravaginal catamenial devices. More precisely the invention relates to a digital tampon having a shaped profile providing a variable cross section.

BACKGROUND OF THE INVENTION

Absorbent tampons for catamenial purposes have been used for decades. Two types of tampons are present on the market, digital tampon and tampon requiring an applicator. Typically, digital tampons are formed by radial compression of a blank with a set of jaws while applicator tampons are formed by moulding a blank. Both types of tampon have generally a cylindrical shape, and both have advantages and disadvantages.

Digital tampon can be inserted manually without an applicator, they have a neat smooth surface; however, the compression column created by the press jaw within the tampon pledget to generate the rigidity required for digital insertion may be uncomfortable for some consumers. Applicator tampons may not have this rigidity issue however they require the use of an applicator and generate additional waste.

It is also important to consider that a tampon may change in position while in place depending on the activity of the wearer, e.g. moving, doing sports or even coughing. This can create discomfort and even leakage if the new position of the tampon is not adapted.

Leakage avoidance and wearing comfort are two important benefits for the consumer.

Shaped tampons have been proposed to fulfill these requirements. These existing shaped products are claimed to match more precisely the wearer anatomy and thus provide a better protection against by pass leakage, reduce discomfort and generally stay in place more efficiently within the vagina.

U.S. Pat. No. 9,622,919B2 by Johnson & Johnson GmbH discloses a process for forming shaped tampon with a radial forming process starting from an intermediate blank. The semi-finished tampon pledget is pushed into a mold to obtain its final shape through expansion. Several alternative shapes are disclosed. Compressed pledged may contain grooves but U.S. Pat. No. 9,622,919B2 is silent about the effect of controlled expansion on grooves.

EP2712594B1, EP2712595B1 & EP2712596B1 by Johnson & Johnson GmbH disclose digital tampons with deep intersecting grooves. Said grooves are continuous in EP2712595B1 or detached in EP2712596B1, or in EP2712594B1 could represent 150% of the pledget length. EP2712594B1 further disclosed an embodiment with a post processing steps in which grooves are formed with finishing mold or calendering rollers. Disclosed tampons are cylindrical and have a circular cross section.

EP1680062A1, EP1686941A1, EP1485053B1, EP1485054B1 and EP1485055B1 by Procter & Gamble purport to disclose tampon with a serpentine shaped outer surface. The tampon has an insertion end region; a withdrawal end region; and a center region. The insertion end region has an insertion end fiber density. The withdrawal end has a withdrawal end region fiber density. The center region has a center region fiber density. The insertion end region fiber density is greater than the center region fiber density. The shaped tampons disclosed have varying average fiber density regions. Grooves pattern are not discussed and tampons with a non-circular cross section are not disclosed.

U.S. Pat. No. 8,684,987B2 by Procter & Gamble purports to disclose a self-orienting tampon having a non-circular cross-section. The tampon includes a self-sustaining, fluid-expanding, compressed absorbent pledget having one or more absorbent materials. The tampon has a width, a thickness, and a length. The width can be greater than the thickness and an aspect ratio of the width to the thickness can be from greater than about 1.4:1 to less than about 2.0:1. Grooves pattern or curved profile of the outer surface along the longitudinal length are not disclosed US20040199137A1 by Peter J. B. Lamb purports to disclose a tampon which includes an elongate absorbent body which is non-circular in outline in end view. US20040199137A1 further discloses a tampon which has an angular orientation relative to its longitudinal axis. Groove pattern or curved profile of the outer surface along the longitudinal length are not disclosed.

U.S. Pat. No. 8,474,114B2 by Ruggli Projects purports to disclose a method for a shaping step completing a process for producing a tampon which is produced of an absorbent material. At least one groove is embossed onto the peripheral surface by radially compressing at least one region of the tampon extending along a peripheral surface of the tampon, the groove plane substantially extending normal to the longitudinal extension of the tampon. Cross section perimeter and outer surface profile are not discussed. Longitudinal groove patterns are not disclosed.

U.S. Pat. No. 5,370,633A by Josue J. Villalta purports to disclose an anatomically shaped tampon. The main body has a pair of side ridges connected to an intermediate wall forming an external configuration resembling a capital H. One end of the tampon includes an outwardly opening cavity to fittingly receive the uterine cervix limiting movement of the tampon. Cross-section remains the same along the tampon pledget length. Particular cross section and outer surface profiles are disclosed. Grooves pattern are not mentioned.

Despite all the shaped tampons proposed in the prior art there is still a need to address the major concerns of the consumers: wearing comfort and leakage avoidance.

SUMMARY OF THE INVENTION

The present invention is proposed to solve these problems by providing shaped tampons that are adapted to the feminine anatomy and shows good fluid absorption properties.

Accordingly, the present invention relates to a shaped tampon with a groove pattern and a combination of external shapes varying radially and longitudinally.

In a first aspect the shaped tampon according to the present invention, having a longitudinal axis, an insertion portion with an insertion tip, a withdrawal portion with a withdrawal end, the insertion and withdrawal portions being converging through a central portion, and each portion comprising a plurality of grooves, characterized by the contour of said insertion portion in an axial cross section plane being an ellipse, the said ellipse having a major axis and a minor axis, wherein the major axis is not equal to the minor axis; and a maximal axial cross section, and the contour of said insertion portion is curved in at least one longitudinal cross section plane, the grooves on said insertion portion extend from the central portion to the insertion tip and are merged in a dome shaped insertion tip.

In a second aspect, the shape of the tampon according to the present invention provides a guided insertion to ease the correct and comfortable positioning.

In a third aspect, the tampon according to the present invention have a higher expending portion on the insertion portion of the tampon pledget and thus most of the absorption occurs in an area where the vagina is less sensitive, increasing the consumer wearing comfort.

In a fourth aspect, the tampon according to the present invention is flexible and provides an increased wearing comfort despite its structural strength that is required to be stable when inserted digitally.

DETAILED DESCRIPTION OF THE INVENTION

As used in the specification and the claims, the term "pledget" and variants thereof relate to a pad or a compress of absorbent material such as fibers designed to absorb bodily fluids. A "tampon pledget", or "absorbent tampon pledget", relates to the compressed absorbent material after compression of a tampon blank in a press.

Figure 1:
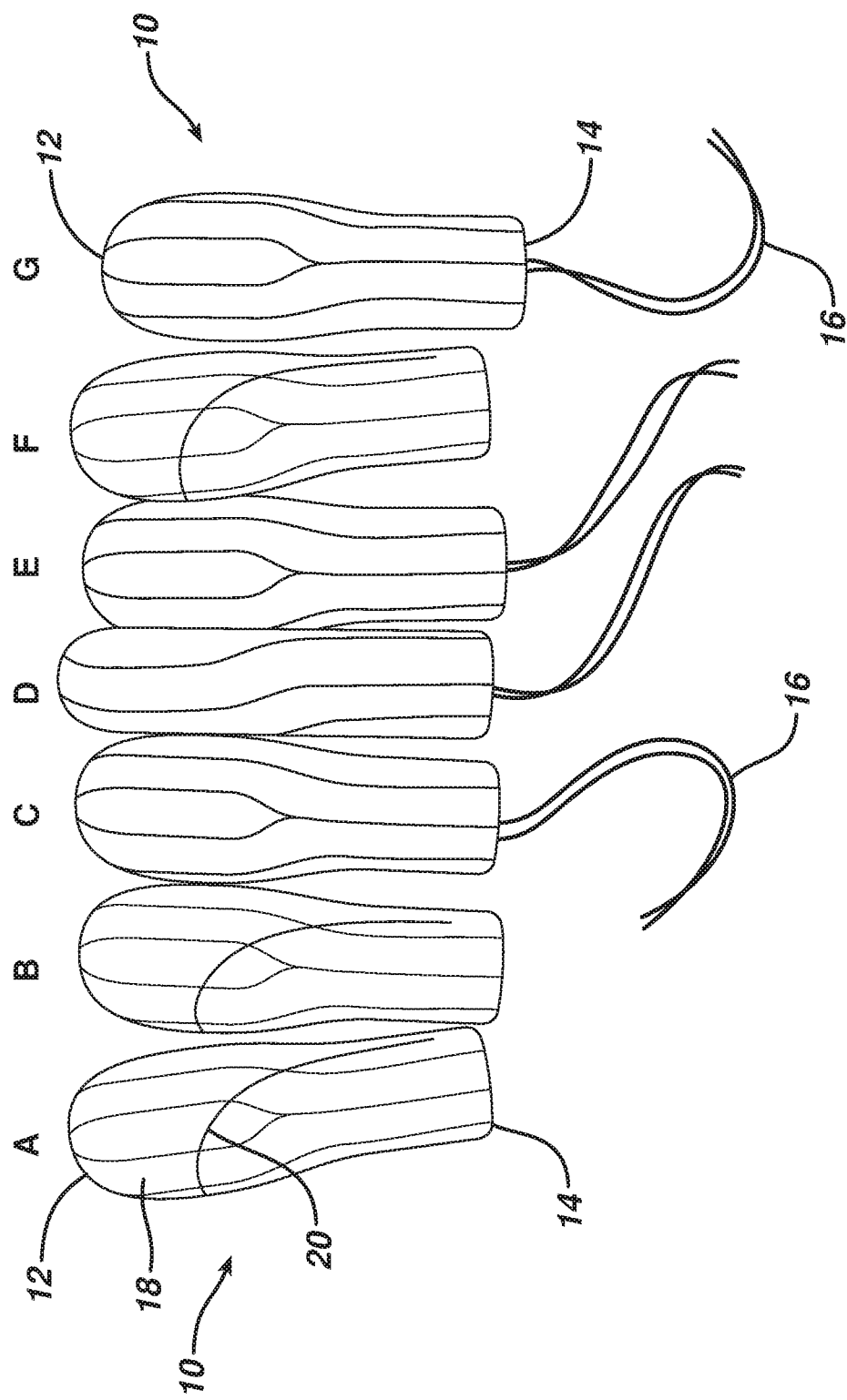
FIG. 1 is an illustration of a series of 6 tampons according to one embodiment the present invention. Tampons are identified by a letter, from A to G, from the left to the right side of the picture.

As shown in FIG. 1, a shaped tampon 10 is an elongate compressed fibrous pledget extending from a rounded insertion portion 12 to a withdrawal portion 14 having a withdrawal string 16 extending therefrom. These may be enclosed in a primary packaging 18 having a line of weakness or tear line 20 to enable opening of the wrapper 20 for removal of the enclosed tampon 10. The series of tampon views illustrates the rotation of an exemplary tampon through approximately 180° and illustrates the shaping and changing cross-section dimensions around the tampon. Tampons A, B, C, E, F, G views shows the larger side of their insertion portion. Tampon D view shows the smaller side of its insertion portion. Tampons A, B and F are wrapped in a primary packaging 18. Tear line 20 for opening of said packaging are indicated by a black curved line. Tampons C, D, E and G are not wrapped. Withdrawal string 16 from each tampon is lying respectively below the withdrawal portion 14 of each unwrapped tampon 10.

Figure 2:
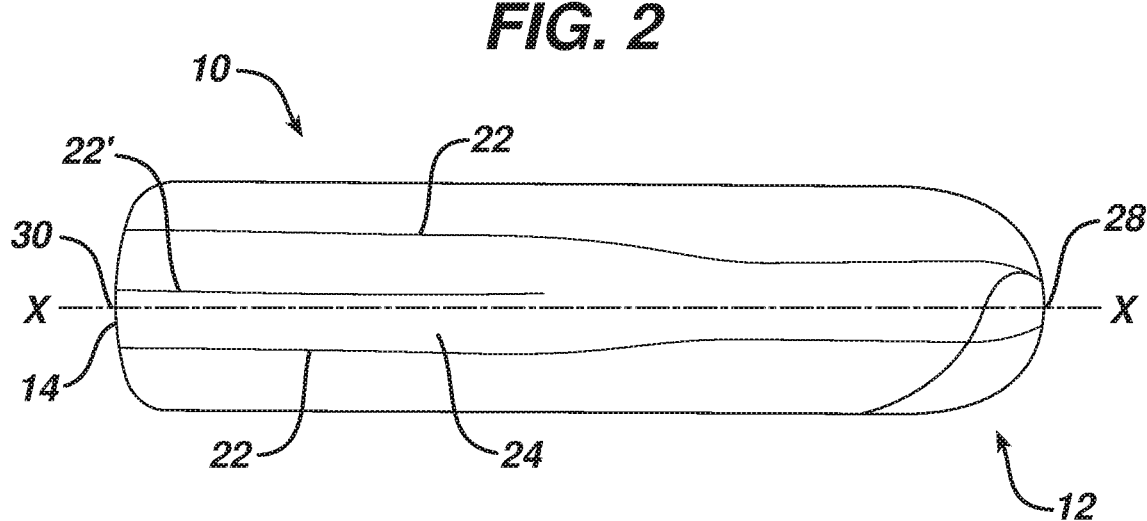
FIG. 2 is side view of a wrapped tampon.
Figure 3:
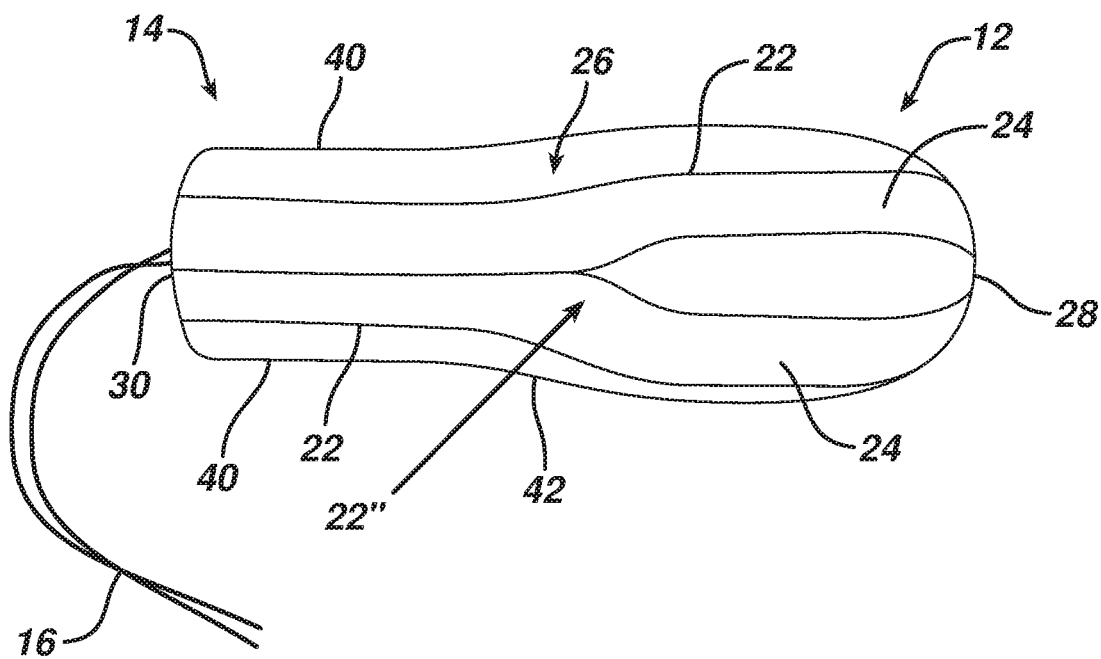
FIG. 3 is front plan view of the tampon in an unwrapped configuration with a withdrawal string extending therefrom.

FIG. 2 is side view of a wrapped tampon 10. This shows the side profile of the insertion portion 12, and FIG. 3 shows the front plan view of the tampon 10 showing the larger profile of the insertion portion 12. The tampon 10 of FIGS. 2 and 3 have a plurality of longitudinally extending grooves 22 with ribs 24 disposed therebetween. FIG. 2 illustrates a truncated groove 22', and FIG. 3 illustrates a bifurcated groove form 22". The combination of the bifurcated groove 22" and the truncated groove 22' enables compression as described in co-pending application entitled "Tampon press," filed on even date herewith (Docket No. J&J6003USPSP1), the disclosure of which is herein incorporated by reference, to provide the unique elliptical cross-section of the insertion portion 12 of the present tampon 10.

The outer ellipse shape represents the perimeter of the tampon insertion portion 12. The eight lines orthogonal to the oval perimeter are representing the positions of the grooves 22 on the insertion portion 12.

The circle represents the perimeter of the tampon withdrawal portion 14. The eight lines orthogonal to the circular perimeter are representing the positions of the grooves 22 on the withdrawal portion 14.

Figure 4:
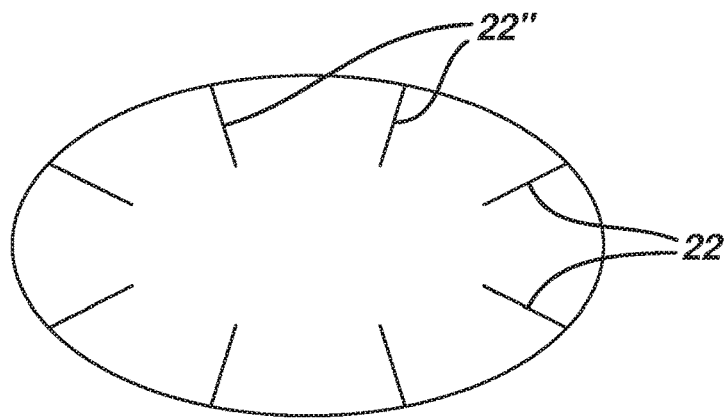
FIG. 4 is a drawing representing an axial cross section view of the insertion portion of a tampon according to the present invention.
Figure 5:
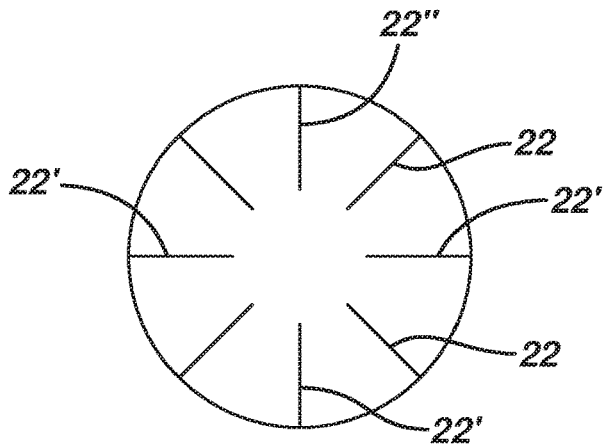
FIG. 5 is a drawing representing an axial cross section view of the withdrawal portion of a tampon according to the present invention.
Figure 6:
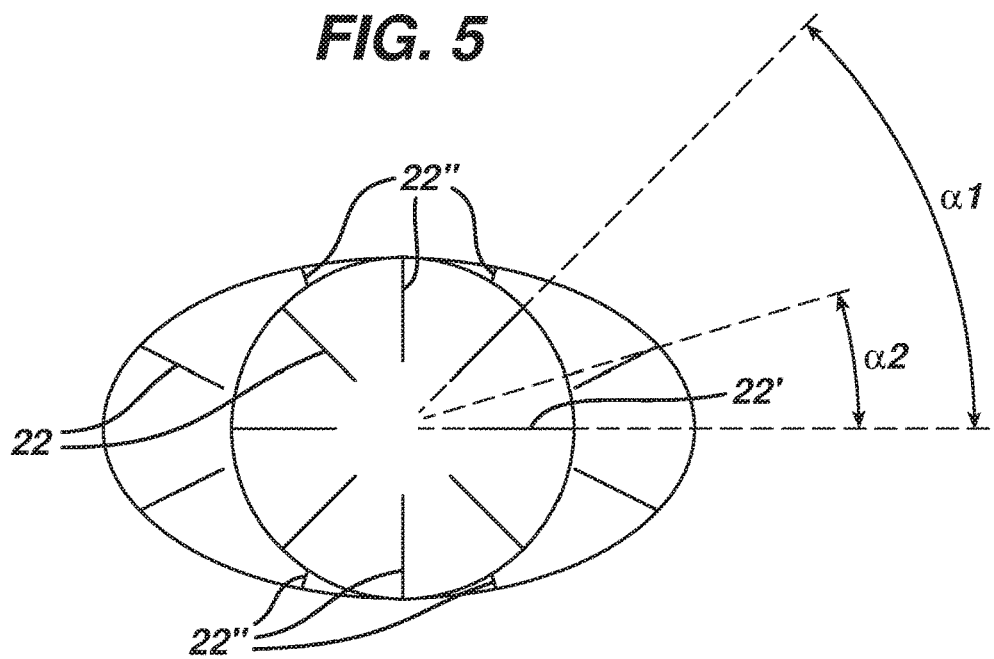
FIG. 6 is a drawing representing a superposition of the axial cross section views of the insertion portion and the withdrawal portion of a tampon according to the present invention.
Figure 7:
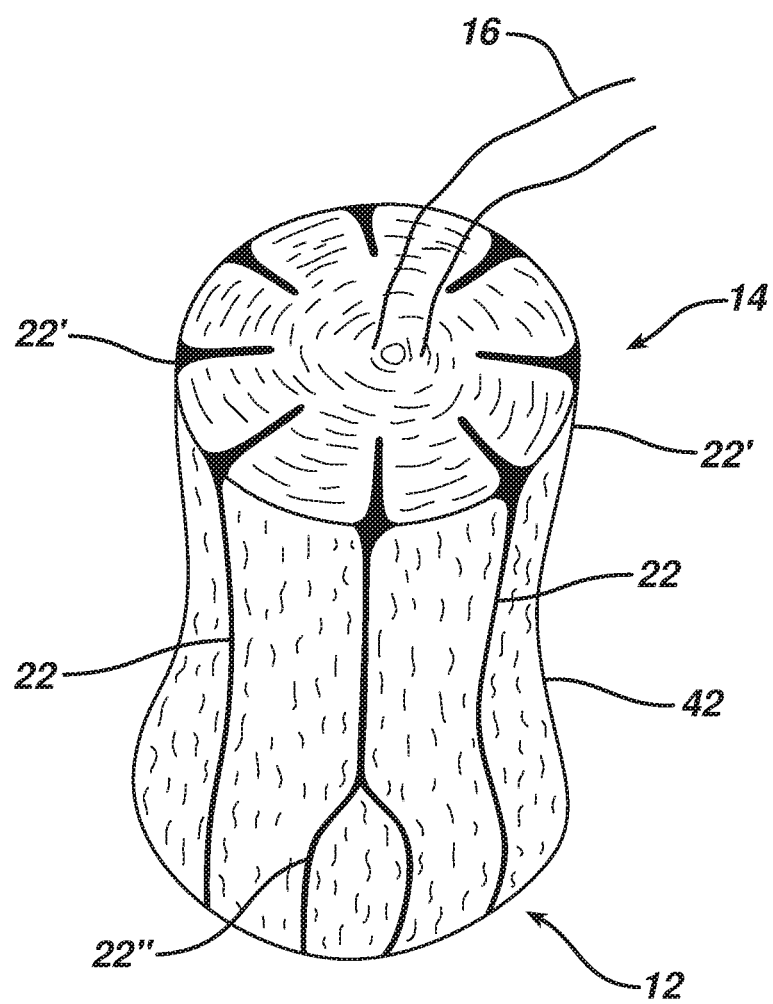
FIG. 7 is a drawing representing a perspective view of a tampon according to the present invention. Insertion tip is pointing backward, down; and withdrawal end is on the foreground. Withdrawal string is also represented, protruding from the withdrawal end.

FIG. 6 is a superposition of FIGS. 4 and 5. Circular withdrawal portion 14 cross-section is at the center and extending outwardly on the sides is the insertion portion 12. Longitudinal axis of the two portions are registered. Positions of the grooves 22 on both insertion and withdrawal portions are represented by the lines orthogonal to either the elliptical or circular perimeters and are grouped to show the bifurcated grooves 22" and the location of the truncated groove 22'.

The present invention discloses shaped tampon, having a longitudinal axis, an insertion portion with an insertion tip, a withdrawal portion with a withdrawal end, the insertion and withdrawal portions being connected through a central portion, and each portion comprising a plurality of grooves, wherein the contour of said insertion portion 12 in an axial cross section plane is substantially elliptical with a major axis and a minor axis and the major axis is not equal to the minor axis. The insertion portion 12 has maximal axial cross section, and the contour of the insertion portion 12 is curved in at least one longitudinal cross section plane. The grooves 22 on said insertion portion 12 extend from the central portion 26 to the insertion tip 28, and they converge toward the domed insertion tip 28.

In the present invention the longitudinal axis X-X of said shaped tampon 10 is defined as the axis passing by the insertion tip 28 and the center of the withdrawal end 30. In the present invention an axial cross section is defined as a plane perpendicular to the said longitudinal axis X-X, shown in FIGS. 4-6.

In the present invention a longitudinal cross section is defined as a plane including the said longitudinal axis.

An ellipse can be defined mathematically as a closed conic section shaped like a flattened circle and formed by an inclined plane that does not cut the base of the cone. An elliptical contour may be as shown on FIG. 4.

This particular shaped profile is believed to be adapted to the vaginal anatomy and to confer a better positioning of the tampon inside of the vaginal cavity as well as an easier insertion. During insertion, positioning and if the consumer changes position while wearing the tampon pledget, the tampon will automatically rotate along its longitudinal axis to match the vaginal wall configuration. This provides improved positioning for the user and can provide a comfort improvement over prior art. The improved positioning can reduce risk of leakage, too.

Also, this particular shape of the tampon according to the present invention may create a higher expending insertion portion on top of the tampon pledget, and thus most of the absorption may occur in an area where the vagina is less sensitive, increasing the consumer wearing comfort The terms "maximal axial cross section" of the insertion portion is defined as the axial cross section for which the perimeter of the insertion portion reaches its maximal value.

In another embodiment of the shaped tampon according to the present invention, the longitudinal opposite sides 40 of the contour of said withdrawal portion 14 according to a longitudinal cross section plane are substantially parallel.

In other words, in this embodiment, the withdrawal portion of the tampon may have a contour of any shape, in an axial section plane, but said contour remain constant when the considered axial cross section plane moves along the longitudinal axis.

In another embodiment of the shaped tampon according to the present invention, the contour of said withdrawal portion according to an axial cross section plane is substantially circular.

In this embodiment, the withdrawal portion of the tampon may have a contour of circular shape, in an axial section plane, but said contour perimeter varies when the considered axial cross section plane moves along the longitudinal axis. For example, the withdrawal portion of the tampon may have an hourglass, a tapered, or a hemispherical shape.

In a preferred configuration, the withdrawal portion may be substantially cylindrical.

In a preferred embodiment of the shaped tampon according to the present invention, the said central portion 28 contains a shoulder 42 at which the insertion portion 12 and withdrawal portion 14 transition.

More precisely the said shoulder may be located between the ¼ and the ¾ of the length of the longitudinal axis of the tampon.

And even more precisely the said shoulder may be located between the ⅓ and the ⅔ of the length of the longitudinal axis of the tampon.

The said shoulder may also be located between the ⅓ and the half of the length of the longitudinal axis of the tampon, wherein said ⅓ designates the first third of the tampon length starting from the insertion tip 28.

In a preferred embodiment, the shoulder may be located substantially at the center of the longitudinal axis of the tampon.

It is believed that these particular proportions between the length of the insertion portion and withdrawal portion create a shaped tampon that will be particularly well adapted to the vaginal anatomy and will help prevent leakage and increase the wearing comfort of the shaped tampon.

In a preferred configuration, the said maximal axial cross section of the insertion portion may be located, along the longitudinal axis, between the said central portion 26 and 10 mm from the insertion tip 28.

Alternatively, in another preferred configuration of the present invention, the said maximal axial cross section of the insertion portion 12 may be located, along the longitudinal axis, between 1 mm and 10 mm from the insertion tip 28.

In a particular embodiment of the shaped tampon according to the present invention, the length of the minor axis of said maximal axial cross section of the insertion portion 12 is equal or inferior to the diameter of said withdrawal portion 14, according to an axial cross section.

The term "minimal diameter" is the distance between the two points corresponding to the intersections of the ellipse minor axis with the ellipses contour.

The term "maximal diameter" is the distance between the two points corresponding to the intersections of the ellipse major axis with the ellipse contour.

It is believed that these proportions between the diameters of the insertion portion 12 and withdrawal portion 14 may create a shaped tampon 10 that would be particularly well adapted to the vaginal anatomy and would help prevent leakage and may increase the wearing comfort of the shaped tampon 10.

In another particular embodiment of the shaped tampon according to the present invention, the minimal diameter of said maximal axial cross section of the insertion portion 12 may be at least equal to the diameter of said withdrawal portion 14, according to an axial cross section.

More particularly, the minimal diameter of said maximal axial cross section of the insertion portion 12 may be equal to the diameter of said withdrawal portion 14, according to an axial cross section.

Alternatively, the minimal diameter of said maximal axial cross section of the insertion portion 12 may be inferior to the diameter of said withdrawal portion 14, according to an axial cross section.

In another configuration of the shaped tampon 10 according to the present invention, the maximal diameter of said maximal axial cross section of the insertion portion 12 may be superior to the diameter of said withdrawal portion 14, according to an axial cross section.

In another embodiment of the present invention, the ratio between the minimal diameter and the maximal diameter of said maximal axial cross section of the insertion portion 12, according to an axial cross section, ranges from 1:1 to 1:4; advantageously from 1:1.5 to 1:2.5; preferably from 1:1.7 to 1:2.0.

These ratios between said minimal diameter and maximal diameter are one of the parameters defining the elliptical shape of the insertion portion 12 axial cross section. These diameters ratios are believed to be well adapted to the vaginal anatomy and would help prevent leakage and may increase the wearing comfort of the shaped tampon 10.

In an embodiment of the present invention at least two, preferably at least four, of the grooves 22 present on the said insertion portion 12 are offset from the grooves 22 present on the said withdrawal portion 14.

According to this configuration, a difference in the groove pattern of the insertion portion and withdrawal portion may be created, this would participate to a discontinuity, e.g., truncated groove 22' and bifurcated groove 22" in the overall groove pattern at the said shoulder location. It is believed to contribute to the longitudinal flexibility of the tampon according to the present invention, thus increasing the wearing comfort of the user.

In a particular embodiment of the present invention at least four grooves present on the insertion portions may be contained within a first set of at least two longitudinal cross section planes, and at least four grooves present on the withdrawal portions may be contained within a second set of at least two longitudinal cross section planes, wherein these at least four longitudinal cross section planes may be distinct from each other.

In other words, the first set of longitudinal cross section planes, as defined above, may not contain a groove located on the withdrawal portion. The second set of longitudinal cross section planes, as defined above, may not contain a groove located on the withdrawal portion.

This particular setup may participate to the discontinuity in the groove pattern at the said shoulder location. It is believed to contribute to the longitudinal flexibility of the tampon according to the present invention, thus increasing the wearing comfort of the user.

In another embodiment of the present invention the number of grooves on the insertion portion is from three to twelve, advantageously from six to ten, more preferably eight.

In another embodiment of the present invention the number of grooves on the withdrawal portion is from three to twelve, advantageously from six to ten, more preferably eight.

In a particular configuration the number of grooves on the insertion portion may be the same that the number of grooves on the withdrawal portion As an alternative, the number of grooves on the insertion portion may be different from the number of grooves on the withdrawal portion In one preferred embodiment, the number of grooves on the insertion portion may be four and the number of grooves on the withdrawal portion may be four.

In another preferred configuration of the present invention, the number of grooves on the insertion portion may be eight and the number of grooves on the withdrawal portion may be eight.

Grooves 22 may be created by the digital tampon manufacturing process when the tampon pledged is compressed by press jaws as described in co-pending application entitled "Tampon press," filed on even date herewith (Docket No. J&J6003USPSP1). This compression creates a column strength required to impart the longitudinal rigidity to the tampon pledget, allowing it to be digitally inserted in the vaginal cavity. The grooves 22 are also believed to help direct the menstrual fluid and help prevent leakage. The number of grooves 22 may be dictated by the manufacturing process, the diameter of the tampon 10.

Thus, the number of grooves 22 may reflect a difference in rigidity for each portion of a tampon, or a difference in the fluid absorption properties of each portion. Grooves may also be a distinctive feature of the tampon pledget, creating a pattern that is recognized by the consumer and helping to differentiate from competitor's tampon.

In an embodiment of the present invention at least two grooves 22 on the insertion portion 12 are converging each respectively to one groove 22 on the withdrawal portion 14, transitioning through the said shoulder located on the central portion 26 from one radial angle $\alpha_1$ to another radial angle $\alpha_2$ (as shown in FIG. 6), to form an offset groove.

In other words, there may be at least two grooves 22 that extend longitudinally from one end of the tampon pledget to the other end, through both insertion portion 12, shoulder 42 and withdrawal portion 14.

In a particular configuration of the invention, four grooves 22 on the insertion portion 12 may be converging each respectively to one groove 22 on the withdrawal portion 14, through the said shoulder located on the central portion 26.

In an embodiment of the present invention at least two pairs of grooves 22" on the insertion portion are converging each respectively to one groove 22" on the withdrawal portion 14 through the said shoulder 42 located on the central portion 26.

In other words, the groove pattern on the shaped tampon may present at least a pair of bifurcated grooves 22" having a "Y" shape. Two grooves on the insertion portion may be converging with one groove on the withdrawal portion. This pattern may be repeated at least twice to provide a pair, or more, of bifurcated grooves 22".

It should be noted that the word "converging" relates to the direction, not to the depth of the groove. The surface appearance of the converging grooves of the shaped tampon according to the present invention may be continuous, but the actual depth of the grooves on each portion may be similar or different and the converging groove would be less deep at the shoulder location that it is on the insertion or withdrawal portions.

An example of a bifurcated groove according to the invention can be seen on FIG. 3.

In a particular configuration of the invention, the said at least two bifurcated grooves may be symmetrical, one on each side of the shaped tampon.

Furthermore, the shaped tampon may have two bifurcated grooves, symmetrical, one on each side of the said tampon.

This very particular construction may participate to the discontinuity in the groove pattern at the said shoulder location. It is believed to contribute to the longitudinal flexibility of the tampon according to the present invention. By longitudinal flexibility it is meant that this specific groove pattern may create an ankle at about the shoulder position. This flexibility of the tampon pledget may be an advantage for the consumer as it would create extra comfort but also it would not interfere with the longitudinal column strength that is required for digital insertion.

In another embodiment the said two grooves on the withdrawal portion that are respectively converging to two pairs of grooves on the insertion portion, are located in a plane that is defined by two axes: the longitudinal axis and the ellipse minor axis, of the said maximal axial cross section of the insertion portion.

In other words, the bifurcated grooves, or "Y" shaped grooves, may be located on the large sides of the shaped tampon as can been seen on FIG. 3.

By "large side" it is meant the side parallel to the major axis of the elliptical cross section of the insertion portion as defined above.

In a particular embodiment the present invention has at least one truncated groove 22' on the withdrawal portion 14 that is not converging to any groove on the insertion portion 12.

In a preferred configuration, at least two grooves 22' on the withdrawal portion 14 are not converging to any groove 22 on the insertion portion 12.

The said at least two truncated grooves 22' on the withdrawal portion 14 located in a plane that is defined by two axes: the longitudinal axis and the ellipse major axis, of the said maximal axial cross section of the insertion portion.

It is another possibility according to the present invention that none of the grooves on the insertion portion may be located in a plane defined by two axes: the longitudinal axis and the ellipse major axis, of the said maximal axial cross section of the insertion portion.

In another configuration, none of the grooves on the insertion portion may be located in a plane that is defined by two axes: the longitudinal axis and the ellipse minor axis, of the said maximal axial cross section of the insertion portion.

In an embodiment of the present invention the grooves 22 on the insertion portion 12 are about evenly distributed.

The grooves 22 on the withdrawal portion 14 may as well be about evenly distributed.

The term "about evenly" should be understood as a regular, or equivalent, spacing between each pair of adjacent grooves with a 0.2 mm, preferably 0.1 mm error margin.

Alternatively, the grooves 22 on the insertion portion 12 may as well be unevenly distributed.

An even distribution of the grooves 22 may be advantageous to achieve a homogenous compression of the fibers, but in some cases the opposite (i.e. uneven distribution) might be desirable to create different compression zone in the same tampon pledget. This might affect the column strength of the tampon and its absorbency properties (capacity, speed).

In a particular embodiment of the present invention, the fiber density of the insertion portion is superior or equal to the fiber density of the withdrawal portion.

In a more precise configuration, the fiber density of the insertion portion may be within 80% to 120% of the fiber density of the withdrawal portion. Or alternatively, the fiber density of the insertion portion may be within 120% to 200% to the fiber density of the withdrawal portion.

This homogeneity in the fiber density along the length of the shaped tampon pledget according to the present invention can be achieved by modifying the amount of raw material in the construction of the tampon blank before compression.

Having a homogenous density may provide an even fluid absorbency along the tampon pledget; but an insertion portion with a higher fiber density may contribute to a higher expending portion on top of the tampon, and thus most of the absorption would occur in an area where the vagina is less sensitive, increasing the consumer wearing comfort.

The present invention also relates to the use of a shaped tampon according to any of the embodiments disclosed above, for collecting catamenial fluids.

What is claimed is:

1. Shaped tampon, having a longitudinal axis, an insertion portion with an insertion tip, a withdrawal portion with a withdrawal end, the insertion and withdrawal portions being connected through a central portion, and each portion comprising a plurality of grooves, a contour of said insertion portion in an axial cross section plane is an ellipse, the said ellipse having a major axis and a minor axis and a maximal axial cross section, and wherein the major axis is not equal to the minor axis;

the contour of said insertion portion is curved in at least one longitudinal cross section plane, and the grooves on said insertion portion extend from the central portion to the insertion tip and are merged in a dome shaped insertion tip, wherein at least 2 pairs of grooves on the insertion portion are converging each respectively to 1 groove on the withdrawal portion through the said shoulder located on the central portion.

2. Shaped tampon according to claim 1, wherein the longitudinal opposite sides of the contour of said withdrawal portion according to a longitudinal cross section plane are substantially parallel.

3. Shaped tampon according to claim 1, wherein the contour of said withdrawal portion according to an axial cross section plane is substantially circular.

4. Shaped tampon according to claim 1, wherein the said central portion contains a shoulder at which the insertion portion and withdrawal portion transition.

5. Shaped tampon according to claim 1, wherein the said maximal axial cross section of the insertion portion is located, along the longitudinal axis, between the said central portion and 10 mm from the insertion tip.

6. Shaped tampon according to claim 1, wherein the minimal diameter of said maximal axial cross section of the insertion portion is equal or inferior to the diameter of said withdrawal portion, according to an axial cross section.

7. Shaped tampon according to claim 1, wherein the ratio between the minimal diameter and the maximal diameter of said maximal axial cross section of the insertion portion, according to an axial cross section, ranges from 1:1 to 1:4.

8. Shaped tampon according to claim 7, wherein the ratio between the minimal diameter and the maximal diameter of said maximal axial cross section of the insertion portion, according to an axial cross section, ranges from 1:1.5 to 1:2.5.

9. Shaped tampon according to claim 8, wherein the ratio between the minimal diameter and the maximal diameter of said maximal axial cross section of the insertion portion, according to an axial cross section, ranges from 1:1.7 to 1:2.0.

10. Shaped tampon according to claim 1, wherein at least two of the grooves present on the said insertion portion are offset from the grooves present on the said withdrawal portion.

11. Shaped tampon according to claim 1, wherein the number of grooves on the insertion portion is from 3 to 12, and the number of grooves on the withdrawal portion is from 3 to 12.

12. Shaped tampon according to claim 11, wherein the number of grooves on the insertion portion is from 6 to 10, and the number of grooves on the withdrawal portion is from 6 to 10.

13. Shaped tampon according to claim 1, wherein at least 2 grooves on the insertion portion are converging each respectively to one groove on the withdrawal portion, through the said shoulder located on the central portion.

14. Shaped tampon according to claim 1, wherein the said 2 grooves on the withdrawal portion that are respectively converging to 2 pairs of grooves on the insertion portion, are located in a plane that is defined by 2 axes:
the longitudinal axis and
the ellipse minor axis, of the said maximal axial cross section of the insertion portion.

15. Shaped tampon according to claim 1, wherein at least one groove on the withdrawal portion is not converging to any groove on the insertion portion.

16. Shaped tampon according to claim 1, wherein the grooves on the insertion portion are about evenly distributed.

17. Shaped tampon according to claim 1, wherein the fiber density of the insertion portion is superior or equal to the fiber density of the withdrawal portion.

* * * * *